(12) United States Patent
Kertser

(10) Patent No.: US 11,529,490 B2
(45) Date of Patent: Dec. 20, 2022

(54) FACIALLY FITTING DEVICES WITH ILLUMINATED PLACEMENT MARKERS

(71) Applicant: Oridion Medical 1987 Ltd., Jerusalem (IL)

(72) Inventor: Michael Kertser, Bney Aish (IL)

(73) Assignee: ORIDION MEDICAL 1987 LTD., Jerusalem (IL)

(*) Notice: Subject to any disclaimer, the term of this patent is extended or adjusted under 35 U.S.C. 154(b) by 1023 days.

(21) Appl. No.: 16/029,783

(22) Filed: Jul. 9, 2018

(65) Prior Publication Data
US 2020/0009344 A1 Jan. 9, 2020

(51) Int. Cl.
*A61M 16/06* (2006.01)
*A61B 5/097* (2006.01)
*A61B 5/083* (2006.01)

(52) U.S. Cl.
CPC ....... *A61M 16/0672* (2014.02); *A61B 5/0836* (2013.01); *A61B 5/097* (2013.01); *A61M 2205/3673* (2013.01); *A61M 2205/587* (2013.01)

(58) Field of Classification Search
CPC .. A61M 2202/0208; A61M 2202/0007; A61M 16/06; A61M 16/0672; A61M 2205/3673; A61M 2205/587; A61M 2205/8256; A61M 16/0666; A61M 16/0677; A61B 5/0836; A61B 5/097; A61B 5/684
See application file for complete search history.

(56) References Cited

U.S. PATENT DOCUMENTS

| | | | |
|---|---|---|---|
| 2005/0061326 A1* | 3/2005 | Payne, Jr. | A61F 5/56 128/206.11 |
| 2010/0113955 A1* | 5/2010 | Colman | A61M 16/0666 600/532 |
| 2011/0027329 A1* | 2/2011 | Guo | A61K 9/0031 424/402 |
| 2014/0026933 A1* | 1/2014 | Kell | H01L 35/30 136/205 |
| 2015/0040896 A1* | 2/2015 | Chodkowski | A61M 16/021 128/202.22 |
| 2016/0106941 A1* | 4/2016 | Hickey | A61M 16/06 128/203.29 |
| 2016/0128141 A1* | 5/2016 | Makosinski | F21V 21/084 315/294 |
| 2016/0279359 A1* | 9/2016 | Chang | A61M 16/0051 |
| 2016/0325123 A1* | 11/2016 | Elliott | G01F 1/28 |
| 2017/0361045 A1* | 12/2017 | Fu | A61M 16/024 |
| 2018/0180381 A1* | 6/2018 | Grace, Jr. | F41G 1/38 |
| 2019/0166933 A1* | 6/2019 | Tiffin | A41D 19/0024 |

\* cited by examiner

*Primary Examiner* — Bradley H Philips
(74) *Attorney, Agent, or Firm* — Cantor Colburn LLP

(57) ABSTRACT

Disclosed herein are facially fitting devices, such as nasal cannulas and oxygen masks, including illuminating placement marker(s), which facilitate correct placement of the facially fitting devices on a face of a subject in dark conditions. The placement marker is powered by a thermoelectric generator, which generates electrical power via thermal coupling thereof to skin on the face of a subject when the facially fitting device is fitted, or partially fitted, on the face of the subject.

20 Claims, 5 Drawing Sheets

FACIALLY FITTING DEVICES WITH ILLUMINATED PLACEMENT MARKERS

TECHNICAL FIELD

The present disclosure relates generally to illuminated consumables, such as illuminated oxygen masks, capnography masks, and nasal cannulas.

BACKGROUND

Facially fitting devices, such as oxygen masks and nasal cannulas may be used for oxygen therapy. Additionally or alternatively, facially fitting devices, such as oxygen masks, capnography masks, capnoxygen masks, and nasal cannulas may be used in conjunction with a capnograph to monitor breathing-related parameters of a subject.

SUMMARY

Aspects of the disclosure, according to some embodiments thereof, relate generally to facially fitting devices, such as oxygen masks, capnography masks, capnoxygen masks, and nasal cannulas. More specifically, but not exclusively, aspects of the disclosure, according to some embodiments thereof, relate generally to facially fitting devices including illuminating placement markers.

The facially fitting devices of the disclosure include one or more illuminating placement markers, which facilitate correct placement of the facially fitting devices on a face of a subject, for example, in non-controlled conditions such as dark conditions (e.g. in the field at night). Advantageously, the placement markers are powered by one or more thermo-electric generators (TEGs), which generate electrical power, via the Seebeck effect, through thermal coupling thereof to skin on the face of a subject when the facially fitting device is fitted, or partially fitted, on the face of the subject.

According to some embodiments, beyond facilitating correct placement, the illumination provided by the placement marker(s) advantageously eases medical intervention operations, such as oral/nasal treatments and device insertion.

Thus, according to an aspect of some embodiments, there is provided a facially fitting device for delivering gas to, and/or collecting gas from, a subject. The device includes:
- A gas port configured to be fluidly connected to an external system for providing and/or collecting gas.
- At least one contact portion, each configured to contact at least one skin surface at, or near, a nose-mouth region, or near a nose, when the device is at least partially fitted on the face of a subject.
- At least one thermo-electric generator (TEG) wherein a first side thereof is exposed or thermally exposed on the least one contact portion, and configured to be powered through a temperature difference between the skin surface and a second side of the TEG.
- At least one light source, powered by the at least one TEG and positioned on the device such as to illuminate the nose-mouth region or the nose, and/or parts of the face on sides of the nose, when the device is at least partially fitted on the face of a subject.

According to some embodiments, the device is a nasal cannula including a main body portion and one or two hollow nasal prongs. Each of the one or two hollow nasal prongs extends upward from the main body portion and is configured to be fitted into a respective nostril of the subject. The main body portion includes the contact portion and the gas port, which is fluidly connected to the one or two hollow nasal prongs.

According to some embodiments, the contact portion contacts a skin surface between the upper lip of the subject and the nose of the subject when the device is at least partially fitted on the face of a subject.

According to some embodiments, the external system is an oxygen source and/or a capnograph.

According to some embodiments, the main body portion further includes a second gas port configured to be fluidly connected to the external system. The main body portion further includes nasal oxygen delivery perforations, fluidly connected to the second gas port. The external system is configured to provide supplemental oxygen via the second gas port and collect exhaled breath via the gas port.

According to some embodiments, the device further includes an oral scoop element adjacent to the main body portion from below. The oral scoop element is configured, when the device is fitted on the face of the subject, to extend over a mouth of the subject, and to collect orally exhaled breath via an oral breath collection opening in the oral scoop element. The oral breath collection opening is fluidly coupled to the gas port.

According to some embodiments, the contact portion measures between about 1 $cm^2$ to about 10 $cm^2$ and is configured to allow providing power to the light source in the range of about 1 µW to about 1 mW.

According to some embodiments, the TEG and the light source are centrally positioned on the main body portion, such as to illuminate the nose from below.

According to some embodiments, the at least one TEG includes two TEGs respectively positioned on a right section and a left section of the main body portion, and the at least one light source includes two light sources respectively positioned on the right section and the left section, such as to respectively illuminate a right part and a left part of the nose-mouth region.

According to some embodiments, the second side of the TEG is exposed or thermally exposed to gas/gas flow on an inner surface of the main body portion. The inner surface defines a passage for gas flow within the main body portion.

According to some embodiments, the device is an oxygen/capnography/capnoxygen mask including a cup member configured to be fitted about the nose-mouth region. The cup member includes the contact portion on a rim of the cup member.

According to some embodiments, the external system is an oxygen source and/or a capnograph.

According to some embodiments, the cup member is transparent or substantially transparent. The at least one TEG includes two TEGs respectively positioned on a right segment and a left segment of the rim. The at least one light source includes two light sources respectively positioned on a right side and a left side of the cup member, such as to respectively illuminate a right part and a left part of the nose-cheek region.

According to some embodiments, the right segment and the left segment each measures between about 1 cm to about 5 cm in length, and are configured to allow providing power to each of the light sources in the range of about 1 µW to about 1 mW.

According to some embodiments, the two light sources are positioned on an inner surface of the cup member or embedded within the cup member.

According to some embodiments, the second side of the TEG is exposed or thermally exposed to air on an outer surface of the cup member or on the rim.

According to some embodiments, the light source is a light-emitting diode.

According to some embodiments, the TEG includes a pair of thermally conducting substrates having sandwiched therebetween at least one pair of n-type and p-type semiconductor legs electrically connected in series.

According to an aspect of some embodiments, there is provided a method of manufacturing a facially fitting device for delivering gas to, and/or collecting gas from, a subject, wherein the facially fitting device is configured to provide illumination through the Seebeck effect. The method includes:

- Providing a facially fitting device including at least one contact portion. The contact portion is configured to contact at least one skin surface at, or near, a nose-mouth region, or near a nose, when the device is at least partially fitted on the face of a subject.
- Incorporating at least one thermo-electric generator (TEG) into or onto the contact portion such that a first side of the at least one TEG is exposed or thermally exposed on the least one contact portion. The TEG is configured to be powered through a temperature difference between the skin surface and a second side of the TEG.
- Incorporating at least one light source, powered by the at least one TEG such as to enable illumination of the nose-mouth region or the nose, and/or parts of the face on sides of the nose, when in use.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. For the sake of clarity, some objects depicted in the figures are not to scale.

In the Figures.

DETAILED DESCRIPTION

Figure 1A:
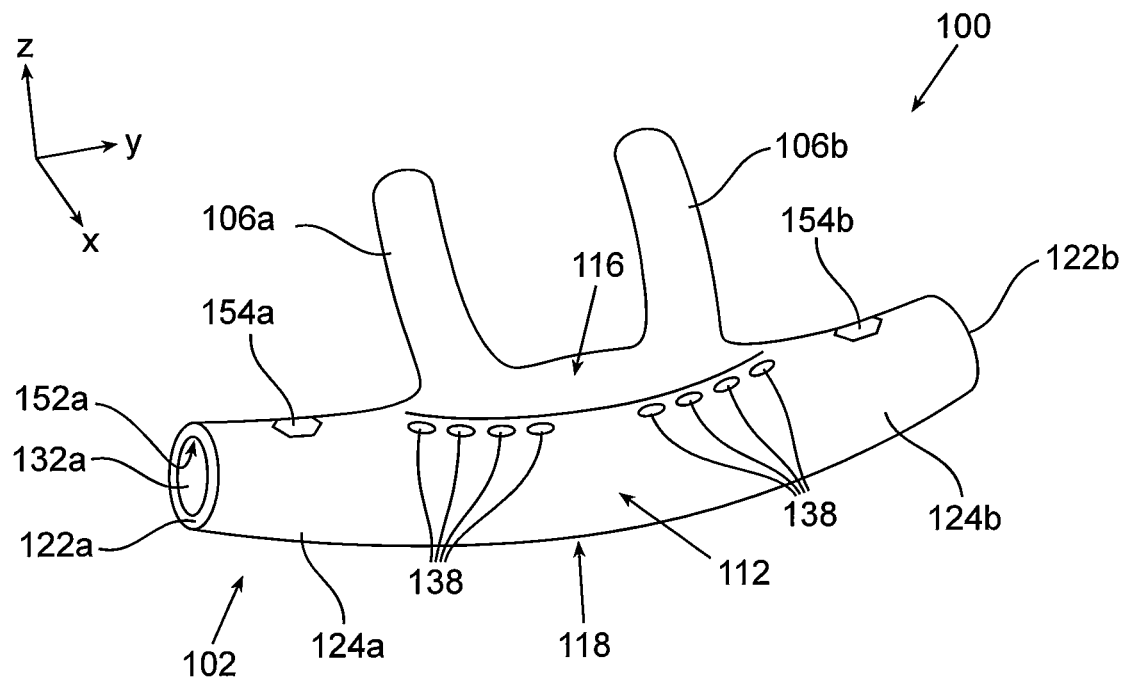
FIG. 1a presents a schematic front view of a nasal cannula including illuminating placement markers, according to some embodiments.

The principles, uses, and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

In the description and claims of the application, the words "include" and "have", and forms thereof, are not limited to members in a list with which the words may be associated.

For ease of description, in some of the figures a three-dimensional cartesian coordinate system (with orthogonal axes x, y, and z) is introduced. It is noted that the orientation of the coordinate system relative a depicted object may vary from one figure to another. Further, the symbol ⊙ is used in the figures to represent an axis pointing "out of the page".

As used herein, the term "about" may be used to specify a value of a quantity or parameter (e.g. the length of an element) to within a continuous range of values in the neighborhood of (and including) a given (stated) value. According to some embodiments, "about" may specify the value of a parameter to be between 80% and 120% of the given value. For example, the statement "the length of the element is equal to about 1 m" is equivalent to the statement "the length of the element is between 0.8 m and 1.2 m". According to some embodiments, "about" may specify the value of a parameter to be between 90% and 110% of the given value. According to some embodiments, "about" may specify the value of a parameter to be between 95% and 105% of the given value.

As used herein, an element, part, or member may be said to be "thermally exposed" to the surroundings thereof or to an external element, part, or member when thermally coupled thereto via an intermediary element, part, or member, which is heat conducting. For example, an inner layer of an element, sandwiched between two outer layers of the element, is thermally exposed to the surroundings of the element when at least one of outer layers is heat conducting (thereby thermally coupling the inner layer to the surroundings of the element). The surroundings may be, for example, air or liquid engulfing the element, or even a second element, adjacent to, and contacting, the element (such that the second element is adjacent to one of the two outer layers, which is heat conducting).

Figure 1B:
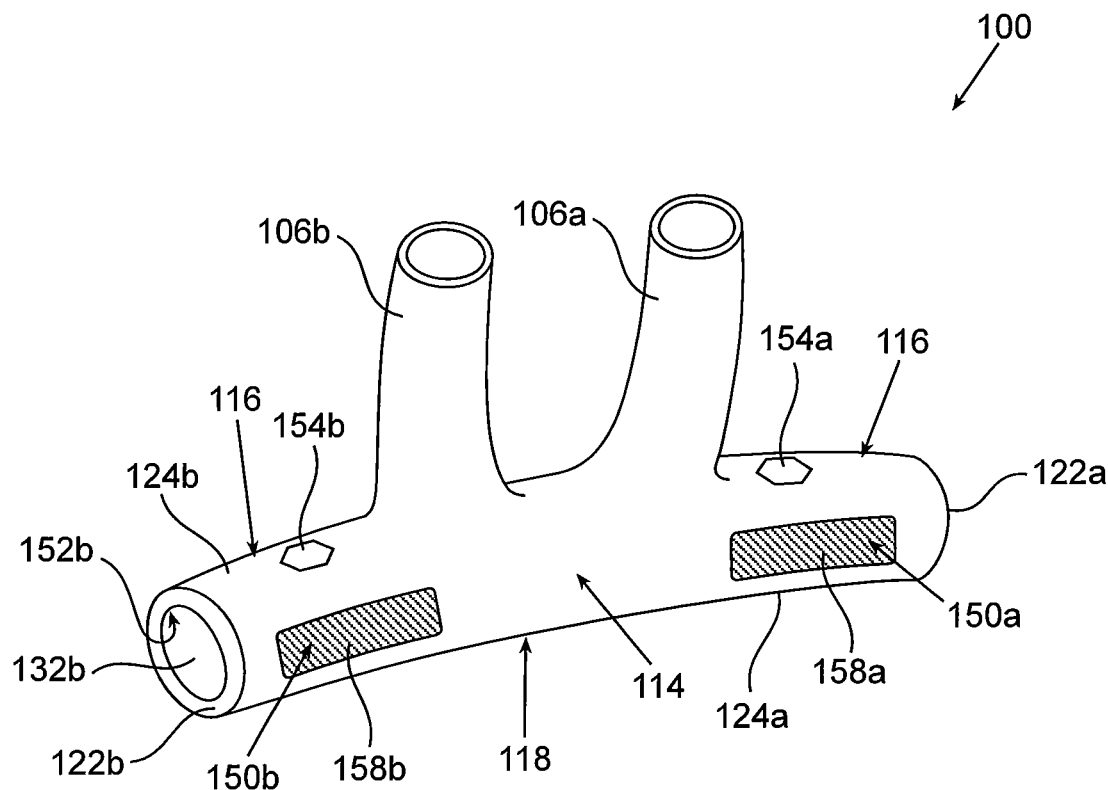
FIG. 1b presents a schematic rear view of the nasal cannula of FIG. 1a, according to some embodiments.
Figure 1C:
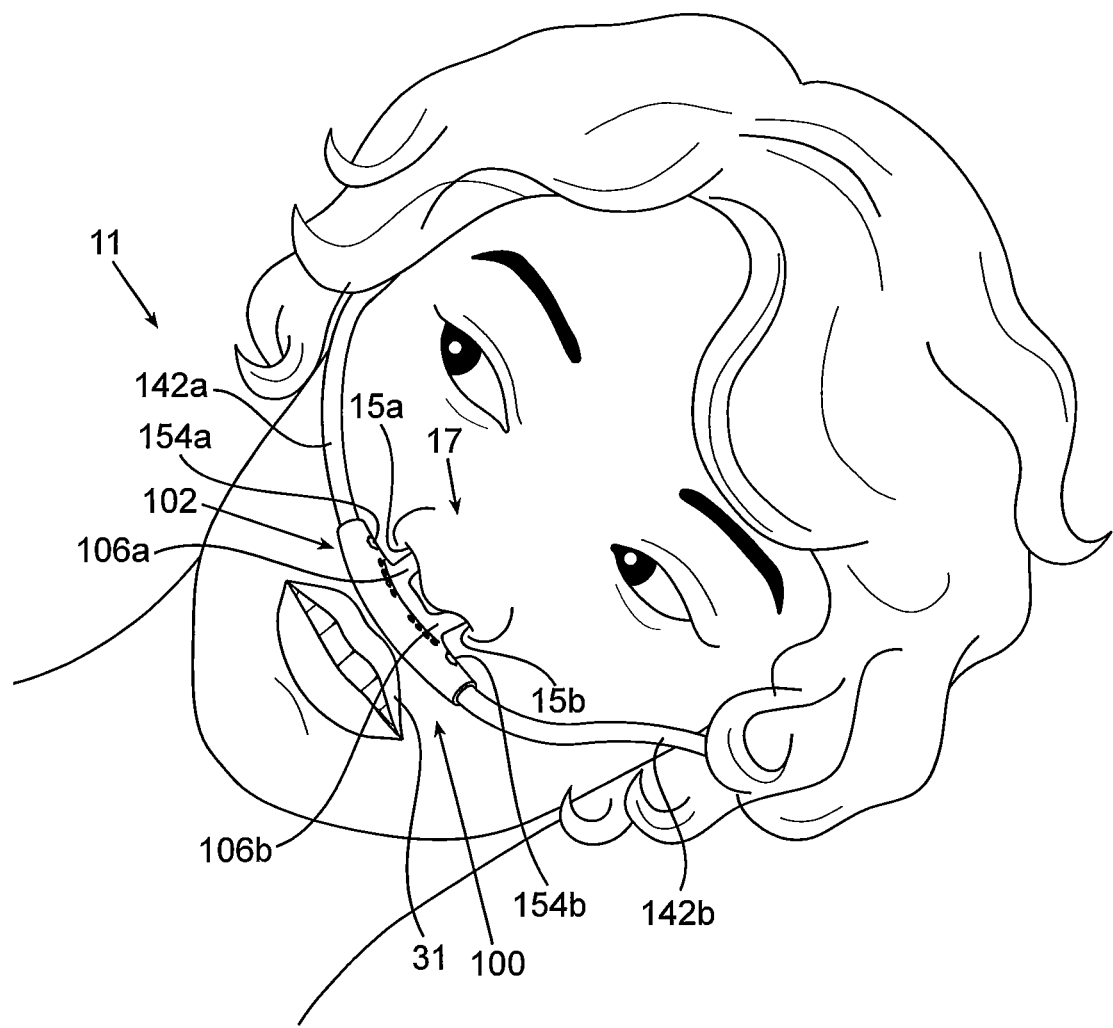
FIG. 1e schematically depicts the nasal cannula of FIG. 1a fitted on the face of a subject, according to some embodiments.

FIGS. 1a and 1b respectively present a schematic front view and rear view of a nasal cannula 100, according to some embodiments. Nasal cannula 100 includes a main body portion 102 and a pair of hollow nasal prongs 106: a right nasal prong 106a and a left nasal prong 106b. According to some embodiments, "right" and "left" with reference to elements/components of nasal cannula 100 are defined from the "point-of-view" of a subject wearing nasal cannula 100, with nasal cannula 100 being configured such that (when worn) right nasal prong 106a and left nasal prong 106b are fitted into a right nostril and a left nostril of the subject (as shown in FIG. 1c). The same applies with respect to elements/components of other embodiments of the present disclosure described in FIGS. 2a-4b. Main body portion 102 may be elongated, having a width (defined along the y-axis) greater than a height and a depth thereof (defined along the z-axis and x-axis, respectively). Each of nasal prongs 106 extends upward (e.g. along or substantially along the z-axis) from main body portion 102 and may be substantially shaped as a tube. Main body portion 102 includes internal passages (channels) configured to allow for gas flow therethrough. The internal passages fluidly connect nasal prongs 106 to one or more gas ports on main body portion 102, as elaborated on below.

As shown in FIG. 1c, nasal cannula 100 is configured to be fitted on a face 11 of a subject, with right nasal prong 106a and left nasal prong 106b respectively fitted into a right nostril 15a and a left nostril 15b of a nose 17 of the subject.

Main body portion 102 includes a front surface 112, a rear surface 114 (shown in FIG. 1b) opposite to front surface 112, an upper surface 116 adjacent to front surface 112 and rear surface 114, and a lower surface 118 opposite to upper surface 116 and adjacent to front surface 112 and rear surface 114. Main body portion 102 includes a right end 122a on a right section 124a of main body portion 102, and a left end 122b on a left section 124b of main body portion 102. It is noted that surfaces 112, 114, 116, and 118 may be curved, e.g. when a cross-section of main body portion 102 is rounded.

When nasal cannula 100 is fitted on face 11, rear surface 114 contacts a nose-mouth region of face 11, between nose 17 and an upper lip 31 at one or more locations in the nose-mouth region. According to some embodiments, all of rear surface 114 contacts skin in the mouth-noise region. According to some embodiments, main body portion 102 may be curved such as to match facial anatomy in the mouth-nose region above upper lip 31. According to some embodiments, one or more parts of rear surface 114 contacts the skin (i.e. rear surface 114 only partially contacts the skin). According to some such embodiments, main body portion 102 includes two contact portions on rear surface 114: a right contact portion located on right section 124a of main body portion 102, and a left contact portion located on a left section 124b of main body portion 102. Main body portion 102 is configured such that when nasal cannula 100 is at least partially fitted on face 11, a right skin surface of face 11 contacts (touches) the right contact portion and a left skin surface of face 11 contacts the left contact portion. (Both the right skin surface and the left skin surface are hidden from view in FIG. 1c due to nasal cannula 100 being fitted on face 11.) The right skin surface may include a skin surface between upper lip 31 and nose 17; the right skin surface may extend below and rightward from, or to the right of, right nostril 15a. The left skin surface may include a skin surface between upper lip 31 and nose 17; the left skin surface may extend below and leftward from, or to the left of, left nostril 15b. According to some embodiments, when nasal cannula 100 is fitted on face 11, the right contact portion and the left contact portion may press against the right skin surface and the left skin surface, respectively.

Right end 122a includes a right gas port 132a. Right gas port 132a may be fluidly connected to nasal prongs 106 (or at least to right nasal prong 106a) via one or more internal passages in right section 124a. Similarly, left end 122b may include a left gas port 132b. Left gas port 132b may be fluidly connected to nasal prongs 106 (or at least to left nasal prong 106b) via one or more internal passages in left section 124b. Each of gas ports 132a and 132b may be configured for gas delivery to/from an external system (e.g. an oxygen source, a capnograph, and so on). According to some embodiments, supplemental oxygen may be delivered via gas ports 132a and 132b. According to some embodiments, supplemental oxygen may be delivered (e.g. by an oxygen source) via right gas port 132a and exhaled breath may be collected (e.g. by a capnograph) via left gas port 132b.

According to some embodiments, main body portion 102 includes nasal oxygen delivery perforations 138 (e.g. on upper surface 116), located proximately to (i.e. near) nostrils 15 when nasal cannula 100 is fitted on face 11. Nasal oxygen delivery perforations 138 are fluidly connected to right gas port 132a, which according to some such embodiments is fluidly decoupled from nasal prongs 106 (which are fluidly coupled to left gas port 132b). Right gas port 132a may be fluidly connected via a first gas tube 142a to an oxygen source (not shown). Left gas port 132b may be fluidly connected via a second gas tube 142b to a capnograph (not shown). In operation, oxygen supplied from the oxygen source flows through right gas port 132a onto nasal oxygen delivery perforations 138, exits therefrom, and is inhaled via nostrils 15. Exhaled breath flows through nasal prongs 106 onto the capnograph via left gas port 132b. A suction pump (not shown) may be used to draw the exhaled breath into the capnograph. According to some embodiments, main body portion 102 includes oral oxygen delivery nasal perforations (not shown) on bottom surface 118.

Main body portion 102 includes at least two thermoelectric generators (TEGs) 150: a right TEG 150a and a left TEG 150b. Each of TEGs 150 is configured to generate electrical power when a temperature difference is present between respective two sides thereof. Each of the TEGs is configured such that when nasal cannula 100 is fitted on a face of a subject, a first side of the TEG is in direct (when exposed on the respective contact portion) or indirect (when not exposed on the respective contact portion) thermal contact with skin in the nose-mouth region (such as to be heated thereby), and the other side of the TEG may maintain a different temperature than the first side. According to some embodiments, the second side of right TEG 150a and the second side of left TEG 150b are embedded within main body portion 102. According to some embodiments, the second side of right TEG 150a and the second side of left TEG 150b may be exposed or thermally exposed to gas (e.g. supplemental oxygen or exhaled breath) or gas flow in internal passages of main body portion 102. For example, the second side of right TEG 150a may be exposed on a right inner surface 152a of main body portion 102 and the second side of left TEG 150b may be exposed on a left inner surface 152b of main body portion 102. Or, for example, the second side of right TEG 150a may be embedded within main body portion 102 such as to be thermally exposed on right inner surface 152a, and the second side of left TEG 150b may be embedded within main body portion 102 such as to be thermally exposed on left inner surface 152b. According to some such embodiments, a layer between the second side of right TEG 150a and right inner surface 152a, and a layer between the second side of left TEG 150b and left inner surface 152b, may include a highly thermally-conductive material or may be perforated. Inner surfaces 152a and 152b may define internal passages within main body portion 102, such as a passage extending to the left from right gas port 132a and a passage extending to the right from left gas port 132b, respectively.

According to some embodiments, the two sides of each of the TEGs may be defined by a pair of thermally conducting substrates. Without being bound to any theory, material or structure, each pair of substrates may, for example, have sandwiched therebetween at least one pair of semiconductor legs, with one of the semiconductor legs being p-type and the other semiconductor leg being n-type (and electrically connected in series to the first leg), as known in the art of TEGs. When more than one pair of semiconductor legs is present, the pairs may be electrically connected in series, such as to increase the overall electrical power generated by the TEG. The semiconductors legs may have high electrical conductivity and low thermal conductivity, as known in the art of TEGs.

Main body portion 102 further includes two light sources 154: a right light source 154a and a left light source 154b. Right light source 154a is powered by right TEG 150a and defines therewith (and electrical wirings and/or connections, not shown) a first electrical circuit. Left light source 154b is powered by left TEG 150b and defines therewith (and electrical wirings and/or connections, not shown) a second electrical circuit. According to some embodiments, light sources 154a and 154b directly contact TEGs 150a and 150b, respectively.

When illuminating, light sources 154 may function as placement markers facilitating correct (accurate) placement (fitting) of nasal cannula 100 on a face of a subject, as explained below.

More specifically, according to some embodiments, right section 124a includes right TEG 150a and right light source 154a, and left section 124b includes left TEG 150b and left light source 154b. According to some embodiments, right TEG 150a includes a right TEG first substrate 158a (i.e. a first substrate of right TEG 150a), a second substrate (not shown), which may be located opposite to right TEG first substrate 158a, and at least one pair of alternately doped (i.e. p-type and n-type) semiconductor legs (not shown) sandwiched between the substrates. Right TEG first substrate 158a is exposed, or at least thermally exposed, on the right contact portion. According to some embodiments, the rest of right TEG 150a is embedded within main body portion 102 (in right section 124a). Similarly, according to some embodiments, left TEG 150b includes a left TEG first substrate 158b (i.e. a first substrate of left TEG 150b), a second substrate (not shown), which may be located opposite to left TEG first substrate 158b, and at least one pair of alternately doped semiconductor legs (not shown) sandwiched between the substrates.

Left TEG first substrate 158b is exposed, or at least thermally exposed, on the left contact portion. According to some embodiments, the rest of left TEG 150b is embedded within main body portion 102 (in left section 124b).

Right TEG 150a is configured such that a respective voltage is generated across each of the semiconductor legs thereof, and an electrical current is induced through the first electrical circuit (thereby causing right light source 154a to illuminate), when a temperature difference exists between right TEG first substrate 158a and the second substrate of right TEG 150a. For example, a temperature difference between right TEG first substrate 158a and the second substrate of right TEG 150a may be induced by bringing into contact the right contact portion and the right skin surface, thereby either (i) bringing right TEG first substrate 158a and the right skin surface into direct thermal contact when right TEG first substrate 158a is exposed on right section 124a (i.e. right TEG first substrate 158a forms part of rear surface 114); or (ii) bringing right TEG first substrate 158a and the right skin surface into indirect thermal contact when right TEG first substrate 158a is embedded within right section 124a (and is adjacent to rear surface 114 which is heat conducting at least along the right contact portion and the left contact portion).

Similarly, left TEG 150b is configured such that a respective voltage is generated across each of the semiconductor legs thereof, and an electrical current is induced through the second electrical circuit (thereby causing left light source 154b to illuminate), when a temperature difference exists between left TEG first substrate 158b and the second substrate of left TEG 150b. For example, a temperature difference between left TEG first substrate 158b and the second substrate of left TEG 150b may be induced by bringing into contact the left contact portion and the left skin surface, thereby either (i) bringing left TEG first substrate 158b and the left skin surface into direct thermal contact when left TEG first substrate 158b is exposed on left section 124b; or (ii) bringing left TEG first substrate 158b and the left skin surface into indirect thermal contact when left TEG first substrate 158b is embedded within left section 124b (and is adjacent to rear surface 114).

According to some embodiments, each of TEG first substrates 158a and 158b defines a contact area with skin in the nose-mouth region measuring between about 1 cm$^2$ to about 10 cm$^2$. According to some embodiments, each of TEGs 150a and 150b is configured to provide power to light source 154a and 154b, respectively, in the range of between about 1 µW to about 1 mW.

According to some embodiments, each of TEG first substrates 158a and 158b is made of, or includes, a highly thermally conducting material, thereby allowing for quick or even substantially immediate illumination when nasal cannula 100 is fitted or partially fitted on a face of a subject. According to some embodiments, each of TEG first substrates 158a and 158b is made of, or includes, silicon-carbide (SiC). According to some embodiments, each of the respective second substrates of TEGs 150 may also be made of SiC.

Right light source 154a may be positioned on, or embedded in, upper surface 116, such that when switched on right light source 154a illuminates at least a right part of the nose-mouth region, particularly, about right nostril 15a, thereby facilitating fitting right nasal prong 106a into right nostril 15a in dark conditions. Similarly, left light source 154b may be positioned on, or embedded in, upper surface 116, such that when switched on left light source 154b illuminates at least a left part of the nose-mouth region, particularly, about left nostril 15b, thereby facilitating fitting left nasal prong 106b into left nostril 15b in dark conditions.

Each of right light source 154a and left light source 154b may be configured to emit light both in the upwards direction and sideways, such as to illuminate the respective right part and left part of the nose-mouth region, and at least partially illuminate upper surface 116, nasal prongs 106, and optionally proximal segments of gas tubes 142a and 142b (shown in FIG. 1c) connected to gas ports 132a and 132b, respectively. According to some embodiments, each of right light source 154a and left light source 154b may be configured to simultaneously emit light in all directions to within about 90° of the positive z axis. According to some embodiments, each of light sources 154 is a Lambertian source.

According to some embodiments, each of light sources 154 is a light-emitting diode (LED). According to some embodiments, right light source 154*a* is positioned near right TEG first substrate 158*a* and left light source 154*b* is positioned near left TEG first substrate 158*b*.

According to some embodiments, the right contact portion and the left contact portion are adjacent, thereby effectively forming a single contact portion. According to some such embodiments, the effectively single contact portion extends over all of rear surface 114.

Figure 2A:
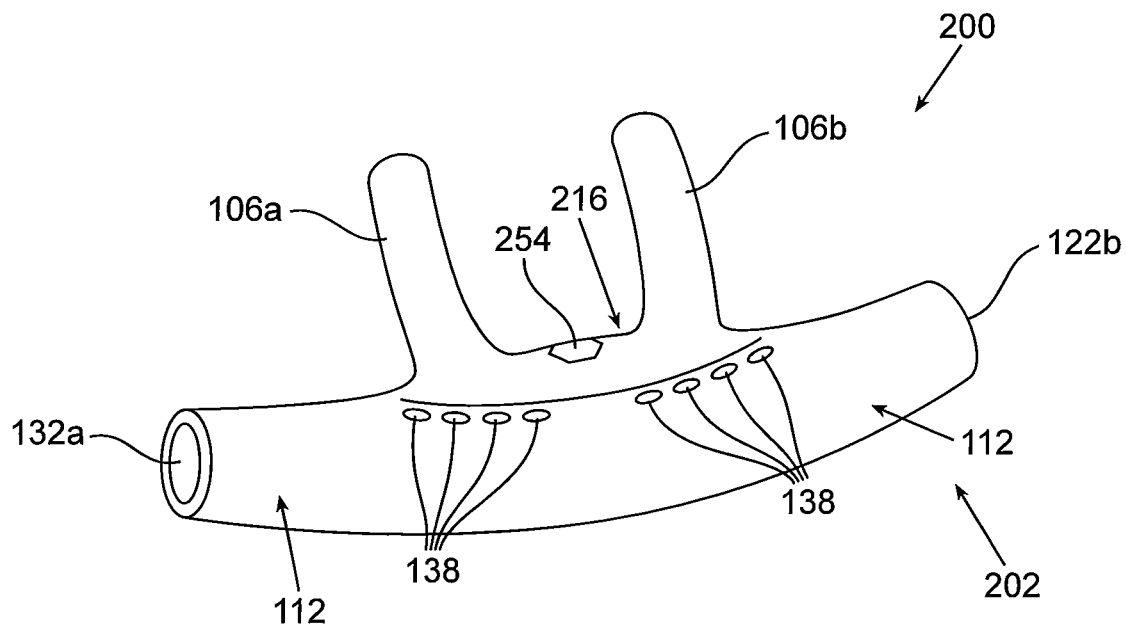
FIG. 2a presents a schematic front view of a nasal cannula including an illuminating placement marker, according to some embodiments.
Figure 2B:
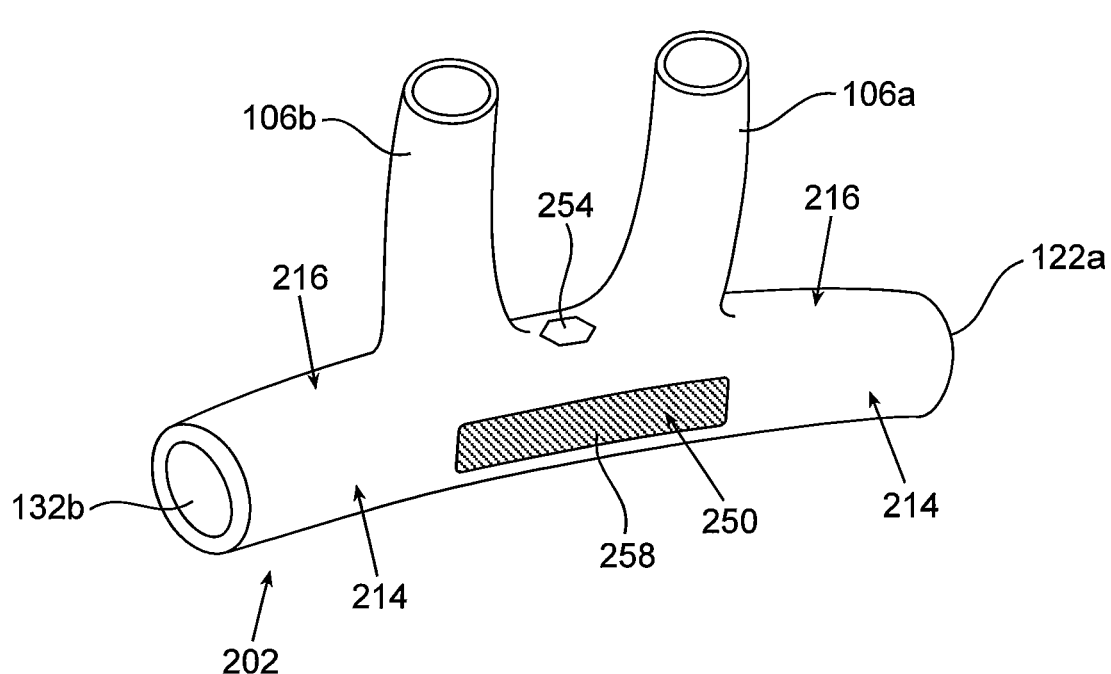
FIG. 2b presents a schematic rear view of the nasal cannula of FIG. 2a, according to some embodiments.

Making reference to FIGS. 2*a* and 2*b*, according to some embodiments, there is provided a nasal cannula 200, which is similar to nasal cannula 100, but which differs therefrom in including a single light source 254 similar to light sources 154. FIGS. 2*a* and 2*b* present a schematic front view and rear view of nasal cannula 200. More specifically, nasal cannula 200 includes a main body portion 202 (similar to main body portion 102) and nasal prongs 106. According to some embodiments, nasal cannula 200 includes a single contact portion on a rear surface 214 of main body portion 202. According to some embodiments, nasal cannula 200 includes a single TEG 250 similar to TEGs 150. According to some such embodiments, light source 254 is configured to illuminate both nostrils when nasal cannula 200 is fitted or partially fitted on a face of a subject, and to illuminate at least in part nasal prongs 106. According to some such embodiments, light source 254 may be centrally located on an upper surface 216 of main body portion 202, being positioned below, or substantially below, the nose, at an equal, or substantially equal, distance from right nasal prong 106*a* and left nasal prong 106*b* when nasal cannula 200 is fitted on a face of a subject.

According to some embodiments, light source 254 is a LED.

Also indicated is a TEG first substrate 258 similar to TEG first substrates 158*a* and 158*b*.

Figure 3:
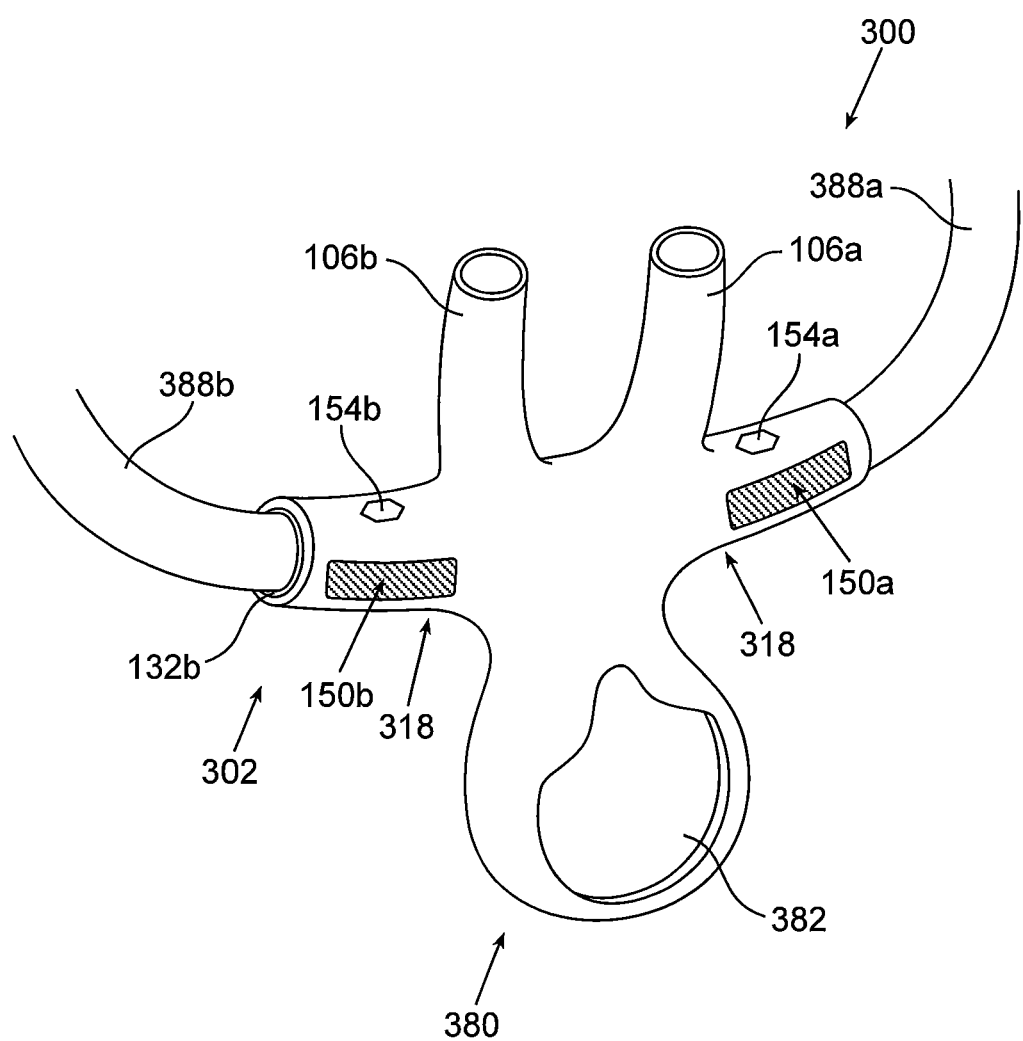
FIG. 3 presents a schematic front view of a nasal cannula, with an oral scoop element, the nasal cannula including illuminating placement markers, according to some embodiments.

Making reference to FIG. 3, according to some embodiments, there is provided a nasal cannula 300, which is similar to nasal cannula 100, but which differs therefrom in additionally including an oral scoop element 380 extending downward from a lower surface 318 of main body portion 302. Oral scoop element 380 includes an oral breath collection opening 382 fluidly coupled to one or both of nasal prongs 106. When nasal cannula 300 is worn, oral scoop element 380 may cover or partially cover the mouth of the subject such that exhaled breath of the subject may be collected via oral breath collection opening 382. According to some embodiments, nasal cannula 300 further includes oral oxygen delivery perforations (hidden from view in FIG. 3) located e.g. on lower surface 318 or an upper part of oral scoop element 380.

Also depicted are gas tubes 388*a* and 388*b* which are connected to right gas port 132*a* and left gas port 132*b*, respectively.

According to some embodiments, nasal cannula 100 may be configured to function solely or primarily as an oxygen nasal cannula. According to some such embodiments, nasal cannula 100 includes a single gas port, e.g. right gas port 132*a* where through supplemental oxygen to is conveyed to nasal prongs 106. According to some such embodiments, both right gas port 132*a* and left gas port 132*b* are configured to convey supplemental oxygen to nasal prongs 106.

According to some embodiments, nasal cannula 100 may be configured to function solely or primarily as a capnography nasal cannula.

According to some embodiments, not depicted in the figures, there is provided a nasal cannula similar to nasal cannula 100, or nasal cannula 200, or nasal cannula 300, but differing therefrom in including a single nasal prong, e.g. similar to right nasal prong 106*a*.

As used herein, according to some embodiments, the terms "right gas port" and "second gas port", with reference to a nasal cannula such as nasal cannula 100 or a nasal cannula similar thereto, are used interchangeably.

Figure 4A:
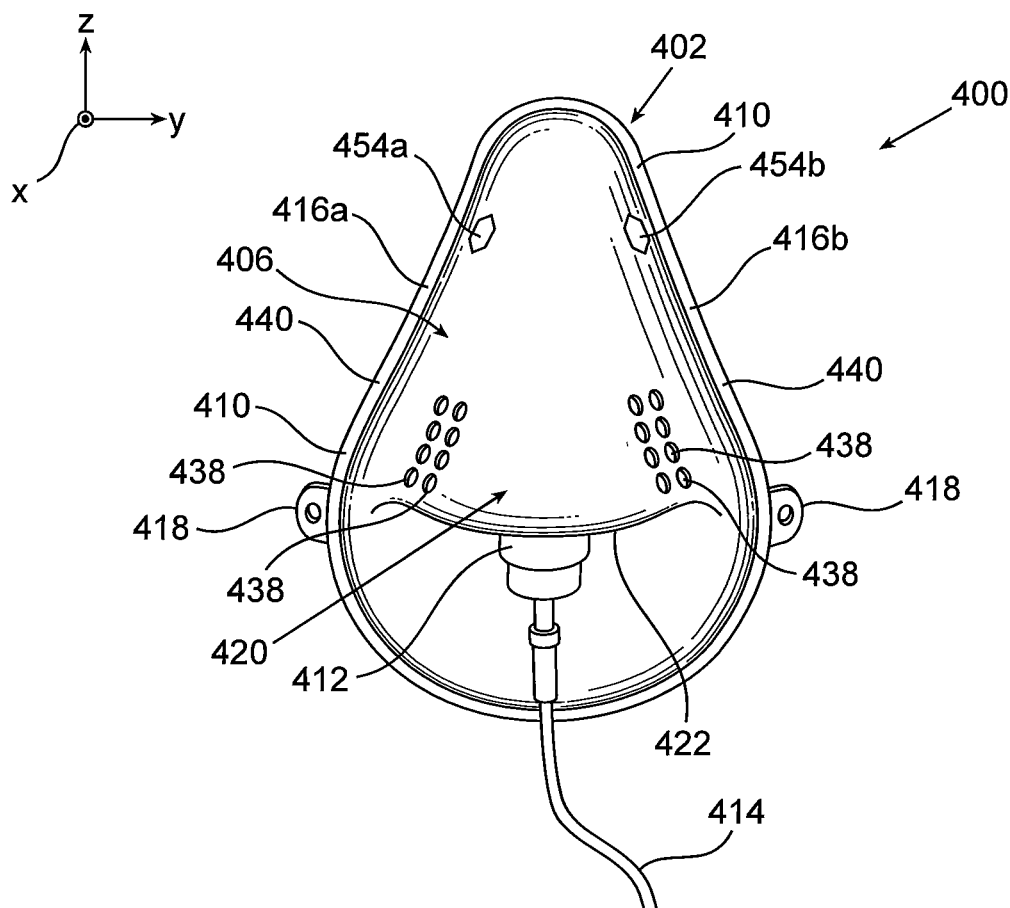
FIG. 4a presents a schematic front view of an oxygen mask including illuminating placement markers, according to some embodiments.
Figure 4B:
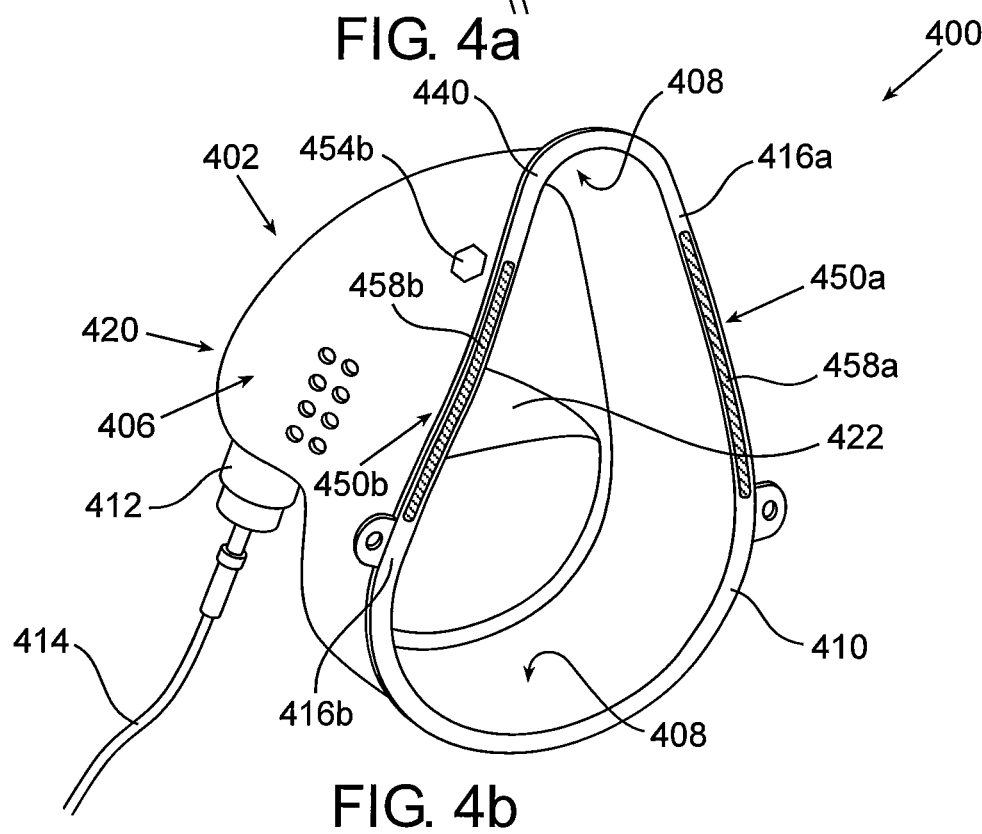
FIG. 4b presents a schematic perspective rear view of the oxygen mask of FIG. 4a, according to some embodiments.

According to an aspect of some embodiments, there is provided an oxygen mask. FIGS. 4*a* and 4*b* present a schematic front view and a perspective rear view of an oxygen mask 400. Oxygen mask 400 includes a cup member 402 configured to fit on a face of a subject such as to cover a nose and potentially also a mouth of the subject. Cup member 402 may generally be rounded, and dimensioned such as to accommodate the nose. Cup member 402 includes an outer surface 406, an inner surface 408, a rim 410, and an oxygen port 412.

When oxygen mask 400 is worn, rim 410 contacts or a least partially contacts the face, at least on a part to the right of the nose and at least on a part to the left of the nose, e.g. on both cheeks or even on the cheek bones. Cup member 402 may include flexible or elastic portions being thereby adaptable to different facial anatomies. In particular, rim 410 may be flexible or elastic or include flexible or elastic portions. More specifically, rim 410 includes at least two contact portions: a right contact portion on a rim right segment (or section) 416*a* and a left contact portion on a rim left segment (or section) 416*b*. According to some embodiments, rim 410 is configured such that when oxygen mask 400 is worn, the right contact portion contacts the right cheek and the left contact portion contacts the left cheek.

When oxygen mask 400 is worn, an inner volume is defined by the space between inner surface 408 and the face. Oxygen port 412 is configured to be connected to an oxygen tube 414. Supplemental oxygen may be delivered via oxygen tube 414 and oxygen port 412 into the inner volume.

Cup member 402 may include a pair of lobe-shaped portions 418 projecting outwardly from rim 410. Oxygen mask 400 may be secured onto the face using one or more straps (not shown), which may be secured to cup member 402 via holes (not numbered) on lobe-shaped portions 418.

According to some embodiments, oxygen mask 400 may also function as a capnoxygen mask, being configured also for sampling exhaled breath of a subject. In such embodiments, cup member 402 may further include an exhaled breath port (not shown), positioned e.g. proximately to oxygen port 412.

Optionally, according to some embodiments, cup member 402 may include a seat-like portion 420. Seat-like portion 420 defines a shelf 422 located below the nostrils when oxygen mask 400 is worn. Shelf 422 includes oxygen port 412, and according to some embodiments, oxygen mask is configured to function/also function as a capnoxygen mask, shelf 422 may further include the exhaled breath port.

Optionally, according to some embodiments, cup member 402 may include perforations 438 (not all of which are numbered). According to some embodiments, perforations 438 facilitate removing exhaled breath from the inner volume.

Rim 410 may include at least one flange-like portion 440 in the form of an edge projecting outwardly (on the yz-plane) from cup member 402. (In FIGS. 4*a* and 4*b* a single flange-like portion is depicted, which extends around all of rim 410.) Flange-like portion 440 may allow for greater rim 410-to-skin contact, particularly on the cheeks, when oxygen mask 400 is worn. The greater rim 410-to-skin contact may enhance the comfort of the subject, as well as potentially allow for increased electrical power generation by one or more TEGs included in rim 410 and exposed or thermally exposed on flange-like-portion 440, as elaborated on below.

According to some embodiments, cup member 402 may be made of a transparent material, such as a transparent plastic, thereby facilitating correct placement of oxygen mask 400 on a face of a subject, as elaborated on below.

Rim 410 includes at least two TEGs 450: a right TEG 450a and a left TEG 450b. Each of TEGs 450 is configured to generate electrical power when a temperature difference is present between respective two sides thereof. Each of the TEGs is configured such that when oxygen mask 400 is fitted on a face of a subject, a first side of the TEG is in direct or indirect thermal contact with skin on the face of the subject, e.g. on the respective cheek, and the other side of the TEG may maintain a different temperature than the first side. According to some embodiments, the second side of right TEG 450a and second side of left TEG 450b are embedded within cup member 402, e.g. within rim 410. According to some embodiments, the second side of right TEG 450a and the second side of left TEG 450b may be exposed or thermally exposed to the air. For example, the second side of right TEG 450a and the second side of left TEG 450b may be exposed on, or thermally exposed via, outer surface 406 or flange-like portion 440 on rim right segment 416a and rim left segment 416b, respectively.

According to some embodiments, the two sides of each of the TEGs 450 are defined by a pair of thermally conducting substrates, essentially as described with respect to TEGs 150 in the description of nasal cannula 100.

Cup member 402 further includes two light sources 454: a right light source 454a and a left light source 454b positioned on the right half (right side) and the left half (left side) of cup member 402, respectively. Right light source 454a is powered by right TEG 450a and defines therewith (and electrical wirings and/or connections, not shown) a first electrical circuit. Left light source 454b is powered by left TEG 450b and defines therewith (and electrical wirings and/or connections, not shown) a second electrical circuit.

When illuminating, light sources 454 may function as placement markers facilitating correct placement of oxygen mask 400 on a face of a subject, as explained below.

More specifically, according to some embodiments, rim right segment 416a includes right TEG 450a with right light source 454a being positioned proximately (i.e. near) thereto, and rim left segment 416b includes left TEG 450b with left light source 454b being positioned proximately thereto. According to some embodiments, right TEG 450a includes a right TEG first substrate 458a (i.e. a first substrate of right TEG 450a), a second substrate (not shown), which may be located opposite to right TEG first substrate 458a, and at least one pair of alternately doped semiconductor legs (not shown) sandwiched between the substrates. Right TEG first substrate 458a is exposed, or at least thermally exposed, on the right contact portion. According to some embodiments, the rest of right TEG 450a is embedded within rim 410 (in rim right segment 416a). Similarly, according to some embodiments, left TEG 450b includes a left TEG first substrate 458b (i.e. a first substrate of left TEG 450b), a second substrate (not shown), which may be located opposite to left TEG first substrate 458b, and at least one pair of alternately doped semiconductor legs (not shown) sandwiched between the substrates. Left TEG first substrate 458b is exposed, or at least thermally exposed, on the left contact portion. According to some embodiments, the rest of left TEG 450b is embedded within rim 410 (in rim left segment 416b).

Right TEG 450a is configured such that an electrical current is induced through the first electrical circuit (thereby causing right light source 454a to illuminate) when a temperature difference exists between right TEG first substrate 458a and the second substrate of right TEG 450a. For example, a temperature difference between right TEG first substrate 458a and the second substrate of right TEG 450a may be induced by bringing into contact the right contact portion and the right cheek, thereby either (i) bringing right TEG first substrate 458a and the right cheek into direct thermal contact when right TEG first substrate 458a is exposed on rim right segment 416a; or (ii) bringing right TEG first substrate 458a and the right cheek into indirect thermal contact when right TEG first substrate 458a is embedded within rim right segment 416a.

Left TEG 450b is configured such that an electrical current is induced through the second electrical circuit (thereby causing left light source 454b to illuminate) when a temperature difference exists between left TEG first substrate 458b and the second substrate of left TEG 450b. For example, a temperature difference between left TEG first substrate 458b and the second substrate of left TEG 450b may be induced by bringing into contact the left contact portion and the left cheek, thereby either (i) bringing left TEG first substrate 458b and the left cheek into direct thermal contact when left TEG first substrate 458b is exposed on rim left segment 416b; or (ii) bringing left TEG first substrate 458b and the left cheek into indirect thermal contact when left TEG first substrate 458b is embedded within rim left segment 416b.

According to some embodiments, each of TEG first substrates 458a and 458b defines a contact area with skin in the nose-mouth region measuring between about 1 cm$^2$ to about 10 cm$^2$. According to some embodiments, each of TEG first substrates 458a and 458b may define a thin strip along rim right segment 416a and rim left segment 416b, respectively, having a length of between about 1 cm to about 5 cm. According to some embodiments, each of TEGs 450a and 450b is configured to provide power to light sources 454a and 454b, respectively, in the range of about 1 µW to between about 1 mW.

According to some embodiments, each of TEG first substrates 458a and 458b is made of, or includes, a highly thermally conducting material (e.g. SiC), thereby allowing for quick or even substantially immediate illumination when oxygen mask 400 is fitted or partially fitted on a face of a subject.

According to some embodiments, wherein cup member 402 is transparent, when oxygen mask 400 is worn, light sources 454 illuminate or partially illuminate parts of the face covered by cup member 402 (and optionally uncovered parts of the face, e.g. adjacent to rim right segment 416a and rim left segment 416b). More specifically, right light source 454a may illuminate a right part of a nose-cheek region (i.e. a part of the right cheek and a right part of the nose) and left light source 454b may illuminate a left part of the nose-cheek region (i.e. a part of the left cheek and a left part of the nose), thereby facilitating fitting oxygen mask 400 on the face in dark conditions. Each of right light source 454a and left light source 454b may be configured to emit light both into the inner volume, defined by cup member 402, and out of the inner volume, such as to illuminate parts of the face covered by cup member 402, as well as parts of the face which are not covered by cup member 402, when oxygen mask 400 is worn. According to some embodiments, light sources 454a and 454b are exposed on outer surface 406 proximately to, or on, rim right segment 416a and rim left segment 416b, respectively. According to some embodiments, light sources 454a and 454b are exposed on inner surface 408 proximately to, or on, rim right segment 416a and rim left segment 416b, respectively. According to some embodiments, light sources 454a and 454b are exposed on both outer surface 406 and inner surface 408 proximately to, or on, rim right segment 416a and rim left segment 416b, respectively. According to some embodiments, wherein cup member 402 is transparent, light sources 454a and 454b are embedded within cup member 402 proximately to, or within, rim right segment 416a and rim left segment 416b, respectively. In such embodiments, due to cup member 402 transparency, the embedded light sources may illuminate the surroundings thereof, e.g. the cheeks and the nose, when oxygen mask 400 is fitted on the face.

According to some embodiments, beyond facilitating correct placement of oxygen mask 400, the illumination provided by light sources 454 may also ease medical intervention operations performed under oxygen mask 400, such as residual liquids removal, oral/nasal treatments, device insertion, etc.

According to some embodiments, each of light sources 454 is a light-emitting diode (LED). According to some embodiments, right light source 454a is positioned near right TEG first substrate 458a and left light source 454b is positioned near left TEG first substrate 458b.

The skilled person will appreciate that oxygen mask 400, or a mask similar thereto, can also function as a capnography mask when oxygen port 412 is additionally or alternatively configured for sampling exhaled breath of a subject.

The skilled person will appreciate that nasal cannulas 100, 200, and 300, and nasal cannulas similar thereto, and oxygen mask 400, and oxygen masks similar thereto, according to some embodiments thereof, may also be used for aerosol therapy/nebulizer therapy.

As used herein, according to some embodiments, the terms "facially fitting device" and "nasal cannula" are interchangeable. According to some embodiments, the terms "facially fitting device" and "oxygen mask" are interchangeable.

As used herein, according to some embodiments, the terms "light source" and "placement marker" are interchangeable.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although steps of methods according to some embodiments may be described in a specific sequence, methods of the disclosure may include some or all of the described steps carried out in a different order. A method of the disclosure may include all of the steps described or only a few of the described steps. No particular step in a disclosed method is to be considered an essential step of that method, unless explicitly specified as such.

Although the disclosure is described in conjunction with specific embodiments thereof, it is evident that numerous alternatives, modifications and variations that are apparent to those skilled in the art may exist. Accordingly, the disclosure embraces all such alternatives, modifications and variations that fall within the scope of the appended claims. It is to be understood that the disclosure is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the disclosure. Section headings are used herein to ease understanding of the specification and should not be construed as necessarily limiting.

What is claimed is:

1. A facially fitting device for delivering gas to, and/or collecting gas from, a subject, the device comprising:
    a gas port configured to be fluidly connected to an external system for providing and/or collecting gas;
    at least one contact portion, each configured to contact at least one skin surface at, or near, a nose-mouth region, or near a nose, when the device is at least partially fitted on the face of a subject;
    at least one thermo-electric generator (TEG) wherein a first side thereof is exposed or thermally exposed on the least one contact portion, and configured to be powered through a temperature difference between the skin surface and a second side of the TEG; and
    at least one light source, powered by the at least one TEG, configured to provide at least one illuminating placement marker and positioned on the device such as to be automatically powered on and to illuminate the nose-mouth region or the nose, and/or parts of the face on sides of the nose, when the device is placed in a worn position.

2. The facially fitting device of claim 1, wherein the device is a nasal cannula comprising a main body portion and one or two hollow nasal prongs;
    wherein each of the one or two hollow nasal prongs extends upward from the main body portion and is configured to be fitted into a respective nostril of the subject; and
    wherein the main body portion comprises the contact portion and the gas port, which is fluidly connected to the one or two hollow nasal prongs.

3. The facially fitting device of claim 2, wherein the contact portion contacts a skin surface between the upper lip of the subject and the nose of the subject when the device is at least partially fitted on the face of a subject.

4. The facially fitting device of claim 2, wherein the external system is an oxygen source and/or a capnograph.

5. The facially fitting device of claim 4, wherein the main body portion further comprises a second gas port configured to be fluidly connected to the external system, and wherein the main body portion further comprises nasal oxygen delivery perforations, fluidly connected to the second gas port, and wherein the external system is configured to (i) provide supplemental oxygen via the second gas port and (ii) collect exhaled breath via the gas port.

6. The facially fitting device of claim 3, further comprising an oral scoop element adjacent to the main body portion from below, the oral scoop element being configured, when the device is fitted on the face of the subject, to extend over a mouth of the subject, and to collect orally exhaled breath via an oral breath collection opening in the oral scoop element, the oral breath collection opening being fluidly coupled to the gas port.

7. The facially fitting device of claim 2, wherein the contact portion measures between about 1 cm$^2$ to about 10 cm$^2$ and is configured to allow providing power to the light source in the range of about 1 µW to about 1 mW.

8. The facially fitting device of claim 2, wherein the TEG and the light source are centrally positioned on the main body portion, such as to illuminate the nose from below.

9. The facially fitting device of claim 2, wherein the at least one TEG comprises two TEGs respectively positioned on a right section and a left section of the main body portion, and the at least one light source comprises two light sources respectively positioned on the right section and the left section, such as to respectively illuminate a right part and a left part of the nose-mouth region.

10. The facially fitting device of claim 2, wherein the light source is a light-emitting diode.

11. The facially fitting device of claim 2, wherein the TEG comprises a pair of thermally conducting substrates having sandwiched therebetween at least one pair of n-type and p-type semiconductor legs electrically connected in series.

12. The facially fitting device of claim 2, wherein the second side of the TEG is exposed or thermally exposed to gas/gas flow on an inner surface of the main body portion; the inner surface defining a passage for gas flow within the main body portion.

13. The facially fitting device of claim 1, wherein the device is an oxygen/capnography/capnoxygen mask comprising a cup member configured to be fitted about the nose-mouth region, the cup member comprises the contact portion on a rim of the cup member.

14. The facially fitting device of claim 13, wherein the external system is an oxygen source and/or a capnograph.

15. The facially fitting device of claim 13, wherein the cup member is transparent or substantially transparent, and wherein the at least one TEG comprises two TEGs respectively positioned on a right segment and a left segment of the rim, and the at least one light source comprises two light sources respectively positioned on a right side and a left side of the cup member, such as to respectively illuminate a right part and a left part of the nose-cheek region.

16. The facially fitting device of claim 13, wherein the right segment and the left segment each measures between about 1 cm to about 5 cm in length, and are configured to allow providing power to the each of the light sources in the range of about 1 µW to about 1 mW.

17. The facially fitting device of claim 13, wherein the light source is a light-emitting diode.

18. The facially fitting device of claim 15, wherein the two light sources are positioned on an inner surface of the cup member or embedded within the cup member.

19. The facially fitting device of claim 13, wherein the second side of the TEG is exposed or thermally exposed to air on an outer surface of the cup member or on the rim.

20. A method of manufacturing a facially fitting device for delivering gas to, and/or collecting gas from, a subject, wherein the facially fitting device is configured to provide illumination through the Seebeck effect, the method comprising:

providing a facially fitting device comprising at least one contact portion, said contact portion configured to contact at least one skin surface at, or near, a nose-mouth region, or near a nose, when the device is at least partially fitted on the face of a subject;

incorporating at least one thermo-electric generator (TEG) into or onto the contact portion such that a first side of the at least one TEG is exposed or thermally exposed on the least one contact portion and configured to be powered through a temperature difference between the skin surface and a second side of the TEG; and incorporating at least one light source, powered by the at least one TEG to provide at least one illuminating placement marker on the device such as to automatically power on and to enable illumination of the nose-mouth region or the nose, and/or parts of the face on sides of the nose, when the device is placed in a worn position.

* * * * *